United States Patent
Beattie (10) Patent No.: US 6,426,183 B1
(45) Date of Patent: Jul. 30, 2002

(54) OLIGONUCLEOTIDE MICROARRAYS: DIRECT COVALENT ATTACHMENT TO GLASS

(75) Inventor: Kenneth Loren Beattie, The Woodlands, TX (US)

(73) Assignee: Kenneth L. Beattie, Crossville, TN (US)

( * ) Notice: Subject to any disclaimer, the term of this patent is extended or adjusted under 35 U.S.C. 154(b) by 0 days.

(21) Appl. No.: 09/134,365

(22) Filed: Aug. 14, 1998

Related U.S. Application Data (63) Continuation-in-part of application No. 08/769,651, filed on Dec. 19, 1996, now Pat. No. 6,156,502.
(60) Provisional application No. 60/009,027, filed on Dec. 21, 1995.

(51) Int. Cl.[7] .............................. C12Q 1/68; C12M 1/36; C07H 21/04

(52) U.S. Cl. ....................... 435/6; 435/287.2; 536/23.1; 536/24.3; 536/25.32

(58) Field of Search .............................. 536/23.1, 24.3, 536/25.32; 435/6, 287.2

(56) References Cited

U.S. PATENT DOCUMENTS

| | | | |
|---|---|---|---|
| 5,204,100 A | | 4/1993 | Carozzi et al. ................ 424/93 |
| 5,436,327 A | * | 7/1995 | Southern et al. .......... 536/25.34 |
| 5,487,985 A | | 1/1996 | McClelland et al. ........... 435/91 |
| 5,700,637 A | | 12/1997 | Southern ........................ 435/6 |
| 5,712,126 A | | 1/1998 | Weissman et al. .......... 435/91.2 |
| 5,962,221 A | | 10/1999 | Caetano-Anolles ............ 435/6 |
| 6,048,695 A | * | 4/2000 | Bradley et al. ................. 435/6 |

OTHER PUBLICATIONS

Lamture, et al. "Direct detection of nucleic acid hybridizaton on the surface of charg coupled device" Nucleic Acids Research, 1994, 22(11)2121–2125.*
Beattie et al., *Clin. Chem.* 41: 700–706 (May 1995).
Welsh et al., *Nucl. Acids Res.* 18: 7213–18 (Dec. 1990).
Williams, *Biotechniques* 7: 762–8 (1989).
Khrapko et al., *FEBS Letters* 256: 118–122 (Oct. 1989).
Yershov et al., *PNAS USA* 93: 4913–4918 (May 1996).

(List continued on next page.)

*Primary Examiner*—W. Gary Jones
*Assistant Examiner*—B J Forman
(74) *Attorney, Agent, or Firm*—Burns Doane Swecker & Mathis LLP (57) ABSTRACT

The present invention provides an improved method for stably attaching a desired compound to a silaceous or silane-containing substrate, in particular a glass, porous silica, or oxidized silicon. This method in certain embodiments provides improvements over conventional methods for attaching desired compounds to silaceous or silane-containing substrate, e.g., glass, porous silica, or oxidized silicon materials, e.g. obviating the need for derivatization (e.g., epoxysilane derivatization) prior to attachment. More particularly, the present invention provides a method for stably attaching a desired compound comprising at least one amine and hydroxyl group (e.g., an aminopropanol containing compound), to a silaceous or silane-containing substrate, preferably underivatized (plain) glass, a porous silica, or oxidized silicon substance. The subject method is especially useful for the attachment of nucleic acid sequences, e.g., oligonucleotide or PCR generated DNA fragments, to glass or other silane-containing substrates to which is stably attached to a desired compound, is useful in any application wherein a compound immobilized to a substrate, e.g., a glass, is useful. Such applications include, by way of example, hybridization analysis, DNA purification, immunoassay, and immunopurification methods.

17 Claims, 7 Drawing Sheets

OTHER PUBLICATIONS

Southern et al., *Genomics* 13: 1008–17 (1992).
Nikiforov et al., *Nuc. Acids Res.* 22: 4167–75 (Oct. 1994).
Lehrach et al., *Genome Analysis*, vol. 1: "Genetic and Physical Mapping," pp. 39–81 (1990).
Doktycz et al., "Genosensors and Model Hybridization Studies," Chap. 10. in *Automation Technologies for Genome Characterization* pp. 205–(Tony J. Geugelsdijk, ed.; John Wiley & Sons 1997).
Zengdegui et al., *Nuc. Acids Res.* 20(2): 307–14 (Jan. 92).
Maskos et al., *Nuc. Acids Res.* 20(7): 1679–84 (Apr. 92).
Beattie et al., *Molecular Biotechnology* 4: 213–225 (Dec. 1995).

* cited by examiner

Plain slides                      Epoxy slides 5 min.   5 min.

15 min.   20 min.

45 min.   1 hr.

2 hrs.

4 hrs.

US 6,426,183 B1

OLIGONUCLEOTIDE MICROARRAYS: DIRECT COVALENT ATTACHMENT TO GLASS

RELATED APPLICATIONS

This application is a continuation-in-part of U.S. Ser. No. 08/769,651, filed Dec. 19, 1996, U.S. Pat. No. 6,156,502 which claims priority to provisional application Ser. No. 60/009,027, filed Dec. 21, 1995. Both of these applications are incorporated by reference in their entirety herein.

Some of this work was performed under NIH Grant 1 P20 HG00665 to KLB at the DNA Technology Laboratory, Houston Advanced Research Center.

FIELD OF THE INVENTION

The present invention relates to the fields of molecular biology and nucleic acid analysis. More specifically, the present invention relates to an improved method for attaching a desired compound, preferably a nucleic acid, to a silaceous or silane-containing substrate, such as a glass, e.g., channel glass, glass slide, quartz, $SiO_2$, porous silica, micromachined silicon, oxidized silicon, or other silanized material, or a solid material coated with any of the above. The invention provides an efficient method for achieving the stable attachment of a desired compound to a silane-containing substrate that obviates the need to derivatize or activate such silane-containing substrate to facilitate attachment.

More particularly, the present invention relates to a method for stably attaching a compound having at least one amine and at least one hydroxyl functional group, e.g., an aminopropanol containing compound, to a silaceous or silane-containing substrate, e.g., plain (underivatized) glass, porous silica, or oxidized silicon. The resultant silane-containing substrate, to which is stably attached said functional group-containing compound, can be used in any application wherein compounds immobilized to silane-containing substrates, e.g., glass (e.g., channel glass, glass slide), quartz, $SiO_2$ porous silica, micromachined silicon, or oxidized silicon materials, or materials coated with the foregoing, are useful. Such methods include, in particular, hybridization, nucleic acid isolation, nucleic acid purification, immunoassay, and immunopurification methods.

BRIEF DESCRIPTION OF THE INVENTION

The present invention provides a method for attaching a compound having at least one amine group and at least one hydroxyl group, to a silane-containing substrate, e.g., a glass, porous silica, oxidized silicon, or other silaceous or silane-containing material. More specifically, the present invention provides a method for attaching an aminopropanol-containing compound to a silane-containing substrate, e.g., a glass, porous silica, oxidized silicon, or a silanized material.

Unlike conventional methods wherein a desired compound is attached to a silaceous or silane-containing substrate, such as glass or porous silica, there is no need in the present invention to derivatize or activate the substrate, e.g., glass (such as previous "epoxysilane activation method") to facilitate attachment. Rather, as discussed in detail infra, the subject invention instead provides a method for the stable attachment of a compound containing at least one amino and hydroxyl functional group to plain, i.e., underivatized, or non-activated glass, porous silica, or oxidized silicon. As discussed in detail infra, both of such groups are involved in the attachment, and are preferably proximate to one another, e.g., within 1 to 6 atoms of one another, and more preferably are comprised on adjacent carbon atoms. This method is particularly useful for attaching derivatized oligonucleotides, in particular 3' or 5' aminopropanol-derivatized oligonucleotides, to silaceous or silane-containing substrates such as glasses, porous silicas, and oxidized silicon.

PREFERRED EMBODIMENTS OF THE INVENTION

The invention provides improved methods for stably attaching desired compounds to a silaceous or silane-containing substrate, e.g., glass (e.g., channel glass, glass slide), porous silica, micromachined silicon, or oxidized silicon material, or a material coated with any of the foregoing.

The invention more specifically provides an efficient method for stably attaching a compound having at least one amine and at least one hydroxyl group, which functional groups provide for the stable attachment of such compound to a silaceous or silane-containing substrate, e.g., a glass, such as channel glass, glass slide, quartz, $SiO_2$, micromachined silicon, porous silica, or oxidized silicon material.

The invention specifically provides an efficient method for stably attaching an aminopropanol-containing compound to a silaceous o r silane-containing substrate, e.g., a glass, porous silica, micromachined silicon, quartz, $SiO_2$, silanized material, or oxidized silicon material.

The invention even more specifically provides an efficient method for stably attaching a desired nucleic acid, e.g., an oligonucleotide, to a silane-containing substrate, e.g., a glass, porous silica, or oxidized silicon, by the following steps:

(i) obtaining a derivatized nucleic acid, e.g., an oligonucleotide, that comprises at least one amine and at least one hydroxyl group (wherein said functional groups are distinguished from the $NH_2$—CO bonds that provide $NH_2$ functional moieties in base-paired DNA's) which functional groups facilitate the attachment of said nucleic acid to a silane-containing substrate; and (ii) contacting said derivatized nucleic acid containing said at least one amine and hydroxyl group with a silaceous or silane-containing substrate, e.g., plain glass, porous silica, or oxidized silicon material under conditions that provide for the stable attachment of such compound to said silane-containing substrate, e.g., plain (underivatized) glass, channel glass, glass slide, porous silica, micromachined silicon, quartz, $SiO_2$, silanized material, oxidized silicon, or a material coated with any of the foregoing.

The invention also specifically provides a method for stably attaching an aminopropanol derivatized nucleic acid, preferably a 3'- or 5'-aminopropanol derivatized oligonucleotide to a silaceous or silane-containing substrate by the following steps:

(i) obtaining an aminopropanol-derivatized nucleic acid, e.g., a 3'- or 5'-aminopropanol derivatized oligonucleotide; and (ii) contacting said aminopropanol-derivatized nucleic acid with a silaceous or silane-containing substrate, e.g., plain glass, porous silica, or oxidized silicon, material, under conditions that provide for the stable attachment of such derivatized nucleic acid to said silane-containing substrate, e.g., plain glass or oxidized silicon.

The invention also provides oligonucleotide arrays that are stably attached to silaceous or silane-containing substrates, e.g., plain (underivatized) glass, or oxidized silicon.

The invention also provides uses of oligonucleotide that are stably attached in arrays to silane-containing substrates, e.g., plain (underivatized) glass, or oxidized silicon, for detection and/or quantification of target nucleic acid sequences.

The invention also specifically provides stable oligonucleotide which comprise 3'-aminopropanol-derivatized oligonucleotides that are stably attached to plain (underivatized) glasses, such as microchannel glass, porous silica, or oxidized silicon materials, and method to use these stably oligonucleotide arrays for detecting target nucleic acids having a complementary sequence.

BRIEF DESCRIPTION OF THE DRAWINGS

FIG. 6A compares the hybridization of the 21-mer target oligonucleotide to epoxysilane and plain glass immobilized oligonucleotide arrays.

FIG. 6B compares stripping and rehybridization of oligonucleotide arrays prepared using epoxysilanized glass and plain glass, following extensive hot water washing of the slides used in 6A experiments.

FIG. 6C compares the time course of hybridization of 9-mer arrays prepared using epoxysilanized glass vs. plain glass.

DETAILED DESCRIPTION OF THE INVENTION

Glossary

Prior to describing the invention in detail, the following definitions are provided.

Glass—In the present invention, glass has its conventional definition, i.e., a ceramic material consisting of a uniformly dispersed mixture of silica (sand), soda ash and lime, often combined with such metallic oxides as those of calcium, lead, lithium, cerium, etc., depending on the specific properties desired. The blend (or "melt") is heated to fusion temperature (approximately 700–800° C.), and then gradually cooled (annealed) to a rigid, friable state, often referred to as vitreous. Technically, glass is an amorphous, undercooled liquid of extremely high viscosity which has the appearance of a solid.

Glasses exist in many forms, including by way of example, plate, sheet, fabric, rods, tubing, pipe, powder, beads, flakes, and hollow spheres. Many types of glasses are known and commercially available, including optical glasses, photochemical glasses, photosensitive glasses. The present invention is intended to embrace the use of any glass or other silanized material that enables the stable attachment of a compound containing both an amino and hydroxyl group, e.g., an aminopropanol-derivatized oligonucleotide.

Preferred glasses for use in the invention include planar glass, channel glass, glass slides, quartz, $SiO_2$, and glasses sold by Galileo®, Clontech, Pierce, Jencons, Hamamatsu, or Litton Industries.

Silaceous Substrate or Silane-Containing Substrate or Material—In the present invention, this refers to a silaceous or silane-containing substrate or material, at least one surface of which comprises or has been treated to expose silanol groups. Examples thereof include the glasses identified above, porous silica materials, micromachined silicon, oxidized silicon materials, and materials coated with any of the foregoing.

Silane—Refers to $S_{in}H_{2n+2}$. Silane-containing compounds or substrates are generally gaseous or liquid compounds of silicon and hydrogen, analogs to alkanes or hydrocarbons. $SiH_3$ is called silyl (analogous to methyl) and $Si_2H_5$ is disilanyl (analogous to ethyl). A cyclic silicon and hydrogen compound having the formula $SiH_2$ is called a cyclosilane. Organo-functional silanes are noted for their ability to bind organic polymers to inorganic substrates.

Silanol—refers to SiOH groups.

Plain or Underivatized Glass or Silanized Substrate—In the present invention, this refers to a glass or silanized substrate, such as a porous silicon that as not been treated by chemical or physical means that introduce additional functional groups to facilitate subsequent attachment. This is in contrast to typical glass or silica immobilization techniques which conventionally pretreat the glass or silica material to facilitate covalent attachment, e.g., by epoxysilane activation. (See, e.g., Beattie et al, *Clin. Chem.*, 41(5):700–706 (1995); and Beattie et al, *Mol. Biotechnol.*, 4:213–225 (1995)).

Stable Attachment—In the present invention, stable attachment of a compound having at least one amino acid hydroxyl group (defined below) refers to the attachment that results when a solution containing such compound is allowed to come in contact with a plain or underivatized glass, porous silica, oxidized silica, or other silane-containing substrate under suitable conditions, typically 15–45° C., preferably ambient, and for a sufficient time, to facilitate the stable attachment to said material, preferably for about 5 minutes to about 15 hours. As discussed infra, preferred solutions for immobilization will typically comprise from about 0.01 to 1000 µM of the compound which is to be attached, and more typically will comprise 5 to 200 µM of the compound.

Stable attachment of the present invention is hypothesized to be covalent and more specifically is proposed to comprise an ester linkage. "Stable attachment " in the present invention refers to the fact that substantially all of the compound bound to the surface (after ambient washing with water to remove non-stably attached compound), "substantially all " means at least 50% thereof, and preferably 90% or more, remains bound to the silaceous or silane-containing substrate after prolonged or repeated washing of the substrate, to which said compound is attached, with hot water. More specifically, "substantially all " means at least 50% of the immobilized compound remains stably attached after washing with water of about 65° C. for about 2 hours.

This attachment is stable at a pH ranging from 2 to 9. The attachment becomes labile at higher pH's, i.e., the linkage becomes slightly labile at pH 10 and more labile at pH 12. The lability of this attachment at basic pH's is consistent with the proposed ester linkage between the attached compound and the silane-containing substrate.

Substantially pure DNA—As used herein, isolated, substantially pure DNA or RNA refers to DNA fragments purified according to standard techniques employed by those skilled in the art, such as that found in Maniatis et al, *Molecular Cloning: A Laboratory Manual*, (1982), Cold Spring Harbor Laboratory Press, Cold Spring Harbor, N.Y.

Substantially Homologous DNA—As used herein, substantially homologous DNA refers to DNA that includes a sequence of nucleotides that is sufficiently similar to another such sequence to form stable hybrids under specified conditions. As used herein, substantially homologous DNA includes DNA that hybridizes under conditions of low stringency.

Probe—As used herein, a nucleic acid probe is a DNA or RNA fragment that includes a sufficient number of nucleotides to specifically hybridize to a DNA or RNA that includes identical or closely related sequence of complementary nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, two single-stranded nucleic acid segments have "substantially the same sequence, " within the meaning of the present specification, if (a) both form a base-paired duplex with the same segment, and (b) the melting temperatures of the two duplexes in a solution of 0.5×SSPE differ by less than 10° C. If the segments being compared have the same number of bases, then to have "substantially the same sequence", they will typically differ in their sequences at fewer than 1 base in 10.

Hybridization Conditions—As used herein refers to DNA molecules that form stable hybrids and are considered substantially homologous are such that the DNA molecules with at least about 60% complementarity form stable hybrids. Such DNA fragments are herein considered to be "substantially homologous". In particular, DNA is substantially homologous to another DNA fragment if the DNA forms stable hybrids such that the sequences of the fragments are at least about 60% complementary.

Stringency Conditions—This refers to the different conditions that are used to facilitate hybridization of a probe nucleic acid sequence to a target nucleic acid sequence.

In general, "low stringency " conditions are conditions that favor hybridization between probe and target nucleic acid sequence containing mismatched bases relative to the probe. Low stringency conditions generally refer to hybridization effected at lower temperature (42° C., e.g., instead of 65° C.) and lower salt concentrations.

By contrast, "high stringency " conditions only facilitate hybridization before a probe and a target nucleic acid sequence containing no mismatched bases, or very few relative to the probe nucleic acid sequence. High stringency conditions typically refer to hybridizations effected at higher temperatures, e.g., about 65° C., or higher salt concentrations. The meaning of "high stringency " and "low stringency " is well known to those skilled in the art. (See, *Molecular Cloning: A Laboratory Manual*, $2^{nd}$ Ed. Sambrook et al, 1987.)

Linker or Spacer—Non-nucleotide or nucleotide chemical residues that can be incorporated between the glass surface and the nucleic acid probe or other substance to be attached.

Oligonucleotide—Short strand of DNA or RNA, which may be chemically synthesized, typically of length up to about 100 nucleotides.

Target nucleic acid—Refers to a nucleic acid sequence which specifically hybridizes to a probe nucleic acid sequence.

Probe nucleic acid—Refers to a nucleic acid that hybridizes specifically to a target DNA in a sample, which may be immobilized to the silaceous or silane-containing substance along with other probe nucleic acid sequences to form an array to which the target nucleic acid sequence can be specifically hybridized.

Protein—compound comprised of amino acids linked by peptide bond, which may or may not be glycosylated, typically at least several hundred amino acids.

Polypeptide—compound that is comprised of a fewer number of amino acids than a protein, also typically linked by peptide bonds, typically around 30 to 100 amino acids.

Oligopeptide—compound that is comprised of fewer amino acids, typically up to 30 amino acids, typically linked by peptide bonds.

Compound Having At Least One Amino and Hydroxyl Group—In the present disclosure, this will refer to a compound having at least one hydroxy and amine functional group, both of which functional groups are necessary to achieve the stable attachment of such compound to a silaceous or silane-containing substrate, e.g., plain glass, porous silica, oxidized silicon, or other silane-containing substrate, which functional groups are preferably located within about 1 to 6 atoms of one another, e.g., within 1 to 6 carbon atoms of one another, more preferably within about 1 to 3 atoms from one another, and most preferably which are located on adjacent atoms, e.g., adjacent carbon atoms, which compound is capable of stably attaching to a silaceous or silane-containing substrate. Preferably, such compounds will comprise at least one aminopropanol group, e.g., a 3'- or 5'-aminopropanol-derivatized oligonucleotide.

Most preferably, the compound will comprise a 3'-aminopropanol derivatized oligonucleotide having the following structure:

Label—In the present invention, this refers to a substituent that enables detection and/or quantification of a desired compound, e.g., a nucleic acid or protein to which it typically is attached. Examples thereof include radiolabels, such as $^{32}P$, $^{33}P$, $^{35}S$, fluorescent tags, chemiluminescent tags, enzymes, ligands, including, e.g., biotin, and chemical groups that are distinguishable by mass or other spectroscopic properties.

DETAILED DESCRIPTION

As discussed, the present invention generally relates to novel and improved methods for the stable attachment of compounds to silaceous or silane-containing substrates, e.g., glasses, such as porous silicas, glass slides, micromachined silicon, quartz, $SiO_2$, oxidized silicon, or other silanized substrates, which for certain preferred embodiments of the invention obviates the need to derivatize or activate the glass, porous silica, oxidized silicon, or other silanized substrate in order to facilitate attachment of such compound. The invention also relates to the products obtained by such methods and uses thereof, in particular, for the detection of target nucleic acids.

Such compounds will comprise at least one amino and hydroxyl functional group, which are preferably separated by at most 1 to 6 atoms, more preferably which are separated by at most 1 to 3 atoms, and most preferably which groups are attached to adjacent atoms, e.g., adjacent carbon atoms. Examples thereof include aminopropanol-containing compounds, and other amino alcohol compounds in which the amino and hydroxy functions are on adjacent carbon atoms:

In the case of peptides and proteins, attachment may be facilitated by serine or tyrosine residues (—OH containing) at the amino terminus of the polypeptide or located adjacent to basic amino acid residues (Lys, Arg).

The compounds that may be attached according to the present invention include any compound that desirably is to be attached to a silaceous or glass or other silane-containing substrate, e.g., the glasses and other materials discussed above. Examples thereof include, by way of example, nucleic acids, in particular oligonucleotides, DNA fragments generated by PCR or other methods, peptides, proteins or polypeptides, e.g., enzymes, antibody molecules, hormones, growth factors, cytokines, receptors, agonists, and antagonists thereof, drugs, ligands, and fragments thereof. In a particularly preferred embodiment, the immobilized compound will comprise a 5'- or 3'-aminopropanol-derivatized oligonucleotide, and most preferably will comprise a 3'-aminopropanol-derivatized oligonucleotide.

The immobilized compound may endogenously comprise at least one hydroxyl and amino group that facilitates direct attachment to a glass support according to the subject methods, or such functional groups may be introduced by synthetic methods, including chemical or enzymatic reactions. Whether such functional groups need to be introduced, and the method for their introduction, will vary dependent on the specific compound that is to be immobilized to the silane-containing substrate.

In the specific case of oligonucleotides, modified phosphoramidites are commercially available for facilitating the introduction of a wide variety of 5'-terminal groups during the final condensation reaction during solid phase synthesis or internally in the chain. Also, methods and materials are known which provide for the introduction of desired groups onto the 3' terminus of oligonucleotides. For example, modified controlled, pore glass supports are commercially available which provide for the introduction of a wide variety of functional groups onto oligonucleotides. In this regard, Glen Research and Clonetech provide a wide variety of modified reagents that provide for the synthesis of oligonucleotides comprising different derivatives. Specific examples thereof include that CPG support available from Clontech ("3'-Amino-ON® CPG") and the C3 and C7 supports available from Glen Research (3'-Amino-Modifier C3 CPG and 3'-Amino-Modifier C7 CPG). (See Zendegui et al, *Nucl. Acids Res.*, Vol. 20:307–314 (1992), incorporated by reference in its entirety herein.)

In a particularly preferred embodiment, a 3'-amino modifier C3 controlled pore glass support will be utilized to introduce an aminopropanol group onto a desired oligonucleotide. This functional group is preferred due to the advantageous positioning of the amino and hydroxyl groups, and the relative simplicity of the solid phase chemistry. In general, such method includes incubating said 3'-amino modifier C3 controlled pore glass support material with concentrated ammonia after the chemical synthesis of an oligonucleotide to generate an oligonucleotide comprising a 3'-aminopropanol group.

During post-synthetic incubation of this support in concentrated ammonia, the Fmoc protecting group is cleaved to generate a primary amine function at the 3' end of the oligonucleotide and a 3'-OH group is simultaneously generated by cleavage of the succinimate linkage to the glass. Since the amine and hydroxy functions are on carbon atoms 2 and 3 in the C3 linker, this results in a 3'-minopropanol-derivatized oligonucleotide.

Alternatively, a hydroxyl and an amine functional group respectively may be attached to carbons 1 and 3 on the 5' end of an oligonucleotide using an AminoModifier II phosphoramidite during the final coupling reaction.

Typically, derivatized bligonucleotides will be produced according to solid phase chemistry. However, solution phase chemistry may also be employed to create these and other types of spacings between the amino and hydroxyl groups located at either the 3' or 5' end.

The reactive groups (hydroxyl and amino) used to attach the oligonucleotide to the silaceous or silane-containing substrate, e.g., glass, may be directly attached to the oligonucleotide. Alternatively, chemical linkers (spacers) may be used to create spacer arms between the reactive groups used to attach the oligonucleotide to the glass surface and the nucleotide sequences of the probe. In some cases, this may enhance the accessibility of the surface-immobilized oligonucleotide probe to the DNA target. For example, mono-, di-, tri-, penta- and hexaethylene glycol phosphoramidites can be used in the chemical synthesis of oligonucleotides to incorporate variable length spacer arms at either the 5' or 3' terminus between the terminal ribose and the hydroxyl and amino-containing substituent, e.g., propanolamine. Another example of a linker or spacer is the classic a basic deoxyribose phosphoramidite. The use of such linkers has been previously described in the literature. (See, e.g., Beattie et al, *Clin. Chem.*, 41(5):700–706 (1995); Maskos et al, *Nucl. Acids Rev.*, Vol. 20(7):1679–1684 (1992); and Beattie et al, *Mol. Biotech.*, Vol. 4:215–225 (1995), which are incorporated by reference in their entirety herein.)

With respect to the use of linkers or spacers, previous results have suggested (Beattie et al, *Molec. Biotech*, 4:213–225 (1995); Beattie et al, *Clin. Chem.*, 41:700–706 (1995), incorporated by reference herein) that, while spacer arms apparently had little influence on hybridization efficiency with target strands up to a few hundred bases, such spacers may enhance hybridization efficiency in the case of larger nucleic acids, e.g., on the order of 500 bases or longer. Therefore, whether spacers are utilized will depend on factors, including the size of the target DNA.

The spacer may also comprise a stretch of nucleotides (between the silaceous or silane-containing substrate and actual probe sequence) that do not share any sequence in the target, thereby providing the desired spacing, without requiring the use of non-nucleic acid linkers. For example, it is possible to utilize a linker comprising a series of repeated nucleotide residues, e.g., thymidine residues, or an alternating sequence of nucleotides and chemical linkers. Such linker spacer sequences preferably are chosen to facilitate appropriate hybridization between target and probe, and avoid spurious hybridization to target.

Also, the sequence and length of the oligonucleotides that are attached to the glass or silanized support may be optimized to enhance hybridization efficiency or to provide sequence specificity. Preferably, the length thereof will range from 4 to 100 nucleotides, more preferably 5 to 80 nucleotides, and most preferably 6 to 50 nucleotides.

As noted previously, the subject methods can be used with different glasses, silaceous and silane-containing substrates or substrates coated with such materials. Suitable examples thereof include, in particular, flat glass, quartz, $SiO_2$, and more expensive microchannel plate materials (available from Galileo), or produced by Tonucci's NCG process (disclosed in Tonucci et al, *Science*, 258:783–785 (1992) and U.S. Pat. Nos. 5,264,722, 5,306,661 and 5,234,594), as well as porous silica, or micromachined silicon materials, e.g., preferably those having pore diameters on the order to of 0.01 to 100 microns, more preferably 0.1 to 20 microns. Also, it may be desirable to use flat or micromachined silicon treated to create an oxide layer on the surface, or one which comprises an oxide layer generated spontaneously by exposure of the silicon to an air environment. Other glasses which should be suitable for use in the invention include soda lime glass, borosilicate glass, and leaded glass, e.g., available from Corning and Shot.

A significant advantage of the subject method is the fact that the silaceous substrate (e.g., glass), or other silane-containing material need not be derivatized or activated to facilitate attachment of a suitably derivatized oligonucleotide or other compound, e.g., 3'-aminopropanol-derivatized oligonucleotide. However, derivatization or activation of the substrate can be used in accordance with convention, for instance to increase the number of silanol groups and enhance reactivity. While no derivatization of the silaceous or silane-containing substrate is necessary, it is advantageous to wash the glass or silanized substrate prior to effecting the attachment reaction. This will facilitate uniform reactions across the surface, including surface derivatization, attachment, and hybridization. The materials used for washing will vary dependent upon the chemical composition of the substrate. For glass, acid cleaning (e.g., about 30–60 minutes with 1N $HNO_3$), followed by washing with an organic solvent, such as ethanol, hexane, xylene, acetone, methanol, butanol, propanol, and mixtures thereof, optionally in a sonication bath, followed by water, may be effected.

In the specific case of 3'-aminopropanol derivatized oligonucleotides, a wide variety of cleaning protocols (with and without acid cleaning, followed by sonication in various organic solvents) have been compared by the present inventor. There was found to be no substantial differences with respect to the efficacy of subsequent attachment or hybridization reactions.

It was found that simple soaking of microscopic slides in hexane, followed by ethanol, and subsequent drying, provided a simple, effective cleaning method which did not require acid washing. Moreover, optimal results were obtained when clean slides were heated in an 80° oven for at least an hour prior to application of the probe containing aliquots. This resulted in smaller droplets with less tendency to spread. However, it is anticipated that the optimal cleaning method may vary dependent upon the specific nature of the glass or other silanized material. Those skilled in the art can determine an effective cleaning method that provides optimal results, e.g., optimal attachment and hybridization efficiency.

It is hypothesized in the case of glass that treatment with an alkali (e.g., 1.0 N KOH) may create additional silanol groups on the surface of the glass, and/or may cause etching, resulting in increased surface area. Both of these effects may enhance attachment efficiency. However, a potential problem associated with alkali pretreatment is the fact that the effects of such treatment on the glass, i.e., on its surface structure and chemistry, may vary from one treatment to the next. Where important, care should be taken to precisely control such effects.

Thus, the silaceous or silane-containing substrate, e.g., a glass, will preferably be washed, e.g., as described supra, prior to attachment of the desired compound, e.g., a 3'-aminopropanol derivatized oligonucleotide. However, as noted, this procedure is optional and is not essential to the efficacy of the subject attachment method.

After the washing and drying steps are optionally conducted, the attachment of a suitably derivatized compound to a silaceous or silane-containing substrate, e.g., plain glass, porous silica, or oxidized silicon material, will be effected in general by dissolving the compound which is to be attached, e.g., an appropriately derivatized oligonucleotide in a suitable solvent, e.g., sterile deionized water, at a suitable concentration, typically ranging from 0.01 to 1000 $\mu$M, more preferably, about 1 to 200 $\mu$M, and most preferably, about 5 to 50 $\mu$M, then contacting said solution to said silane-containing substrate for a sufficient time, typically from about 1 minute to about 15 hours. This solution may comprise salts, typically in amounts ranging from 0 to 5M. The pH of the solution will preferably range from 5 to 9, more preferably about neutral, i.e., a pH of about 6.5–7.5.

As discussed below, the compound which is to be attached to the silaceous or silane-containing material may or may not comprise a label that provides for quantitative detection of the compound attached to the silanized substrate, e.g., plain glass, porous silane, or oxidized silicon. Suitable labels are discussed elsewhere in this application.

It is preferable that such attachment be effected under controlled relative humidity conditions, preferably at saturated relative humidity. To effect attachment, the solution containing the compound which is to be immobilized (e.g., derivatized oligonucleotides) is applied to the glass or other support in discrete aliquots. This may be effected by hand or by automated methods. If the immobilized compound is to be used for analytical purposes, it is desirable that the delivery method result in the precise delivery of a small aliquot of the solution comprising a defined quantity of the compound onto a specific region of the glass or other surface. In the case of oligonucleotide solutions, this can be effected by hand pipetting droplets of a volume ranging from 0.2 to 1.0 μL (microliters) using a PipetMan, provided that regular calibration is effected. (This may be performed by weighing droplets immediately after delivery onto a target surface.)

Also, robotic devices are commercially available for spotting of large numbers of probes onto solid substrates. Care should be taken to ensure that the droplets are delivered to the surface and do not cling to the dispenser tip. It is also advantageous to carefully characterize the drop-to-drop reproducibility of attachment across the array substrate and between replicate arrays, e.g., by use of radioactively labeled probes and a phosphorimager or by use of fluorescently labeled probes and a CCD imaging system.

In some instances, it is difficult to control the attachment of nucleic acids to glass. This may be difficult because of drying when small droplets are delivered to the surface. This is especially problematic if the attachment reaction proceeds relatively slowly (such as the epoxysilica/amine reaction). This phenomena should not be significant to the novel attachment method provided herein given the relative rapidity of the subject attachment reaction. However, this may be problematic in some instances because very small droplets (e.g., 0.01–0.1 μL) may dry within a minute, and during drying the reaction may accelerate because of increased probe concentration and then terminate when the water has evaporated. Also, the droplets may dry unevenly, which may account for the "donut" phenomena commonly seen in conventional microarray experiments.

However, this may be avoided by use of larger droplets (e.g., 2–5 μL). Also, droplet drying can be avoided or minimized by use of high (saturated) relative humidity conditions as described previously. However, a possible problem associated with the use of relatively high humidity conditions is the fact that the probe sample which is applied to the silaceous or silane-containing substrate surface may absorb water, causing the droplets to spread and even coalescence.

Even when large numbers of drops are applied to the glass surface, the drying rate should be constant. Thereby, provided that all drops are allowed to dry, and therefore have equal time for reaction, the quantity of probe attached at each spot will be approximately equal, even over the course of a lengthy robotic spotting operation. Moreover, the effects of droplet drying can be further minimized or potentially avoided altogether by the use of channel glass or porous silicon substrates.

As noted, these potential problems should not be a significant concern in the present invention given the high efficiency of the subject attachment reaction which attaches a suitable amino/hydroxyl functional group derivative oligonucleotide, preferably an aminopropanol derivatized oligonucleotide to a silane-containing substrate, e.g., an underivatized glass.

As discussed above, in order to facilitate attachment, the substrate is contacted with the suitably derivatized compound, e.g., 3'-aminopropanol-derivatized compound, e.g., 3'-aminopropanol-derivatized oligonucleotide for a time sufficient to obtain stable attachment, e.g., a time ranging from at least 1 minute to 15 hours, more preferably 5 to 20 minutes. The preferred temperature for effecting attachment will typically range from 15 to 45° C., and more preferably will comprise ambient conditions. In this regard, it has been observed, using derivatized glass, that attachment and hybridization efficiency is reduced at high temperatures (65° C.).

As noted above, the probe density should be controlled to optimize hybridization efficiency. In order to control attachment density across the surface of the substrate, the attachment reaction may be conducted to completion, using a defined mixture of aminopropanol-derivatized oligonucleotides and aminopropanol-derivatized linkers, which optionally may comprise linkers on the oligonucleotides to improve the accessibility of the surface-immobilized nucleic acid to a target DNA. Typically, drops ranging in size from about 50 pL to 5 μL, of a solution containing from about 0.01 to 1000 μM of the compound (e.g., 3' aminopropanol derivatized nucleic acid) will be applied to the silaceous or silane-containing substrate, e.g., plain glass, porous silica, quartz, micromachined silicon, or oxidized silicon, at a suitable distance from one another, typically, from about 0.01 to 10 mm of one another.

The optimal conditions for effecting attachment depend on numerous factors including (i) stability of linkage effected under different conditions (pH, temperature), (ii) requirements for capping of reactive surface groups to prevent reaction with target DNA during hybridization; (iii) selectivity of attachment reaction, (iv) site to site uniformity of attachment and hybridization within a given array; (v) hybridization properties at varying probe density, including kinetics, specificity/mismatch discrimination, lowest concentration of target required to detect hybridization and upper limit of target length that can yield a hybridization signal; (vi) minimal non-specific binding of target DNA to the surface following various "prehybridization" treatments (separate from "capping reactions"; (vii) requirement of any chemical spacers (linkers) between the surface and the probe; (viii) hybridization efficacy for DNA targets of various lengths; (ix) ability to wash hybridized DNA away and conduct multiple rounds of hybridization; and (x) length of time that oligonucleotide microarrays can be stored before hybridization properties deteriorate, to mention a few important considerations.

In light of the above factors, controls that should be included in characterization and optimization of probe attachment are (i) attachment of underivatized oligonucleotide (for selectivity of covalent attachment at terminal modification versus internal residues), (ii) hybridization of mismatch-containing target DNA (for sequence specificity of hybridization); and (iii) attachment to underivatized surface (to verify that reactive surface groups are involved, when applicable, e.g., in epoxysilane-amine attachment).

In particular, conditions should be controlled, if possible, to precisely control the attachment density and to achieve uniform attachment of probes at different positions within the array. Desirably, the compound attached to the silaceous or silane substrate, e.g., 3'-aminopropanol-derivatized oligonucleotide may comprise a label that enables detection and quantification of precise amount of compound immobilized to the substrate. Such labels include in particular $^{32}$P, $^{33}$P, and $^{35}$S, and the other labels identified above.

After effecting attachment, non-covalently bound and unbound compound and label should be removed by a washing procedure, e.g., by rinsing with water. Ideally the washing step should remove virtually all of non-specifically bound compound prior to hybridization. Prior to effecting hybridization, it is also desirable, in order to minimize non-specific binding, to (i) remove unincorporated label from the target DNA, and (ii) to effect prehybridization using suitable blocking agents.

As described in Beattie et al, *Mol. Biotech.*, 4:213–225 (1995), incorporated by reference in its entirety herein, unincorporated label can be removed using Micron-3 microconcentrator units (Amicon). However, in some instances, it may be difficult to totally remove all unincorporated label.

Also, it is important to effect a prehybridization step with a suitable blocking agent prior to introduction of target DNA. This step minimizes non-specific binding and may also enhance the later removal of hybridized strands using hot water. This may be effected, e.g., by treatment with 10 mM tripolyphosphate. This has been shown to effectively minimize non-specific binding of $^{32}$P-labeled target strands to glass slides. (Beattie et al, *Clin. Chem.*, 41(5): 700–706 (1995), incorporated by reference herein.) Alternatively, prehybridization may be effected. using a dilute solution of dried milk or using Denhardt's solution.

After effecting prehybridization, hybridization may be effected by contacting the immobilized oligonucleotide array with a target nucleic acid containing sample, e.g., target DNA obtained by PCR, dissolved in a suitable hybridization buffer.

Suitable hybridization buffers are well known in the art and vary depending on factors such as the desired stringency of the hybridization. One skilled in the art can readily select a suitable hybridization buffer solution based on known materials and information.

For example, a suitable hybridization buffer comprises the following substituents:

3.3M tetramethylammonium chloride in
50 mM Tris-HCl (pH8)
2 mM EDTA,
0.1% SDS
10% polyethylene glycol.

The concentration of the target DNA may be varied within wide limits ranging from 0.01 to 1000 fmol strands/μL (0.01–1000 nM). A preferred concentration is a concentration of 10–50 fmol strands/μL (10–50 nM), for hybridization on a flat surface.

An aliquot of the hybridization mixture containing the target DNA is applied to the silaceous or silane-containing substrate to which is immobilized the probe oligo nucleic acid, e.g., plain glass, as described above, e.g., by pipetting drops of fixed size thereto to cover all arrayed probes. Thereafter, the hybridization reaction will be allowed to proceed. For example, for a microarray produced on a glass slide this may be effected by covering the slide with a cover slip, and incubating the slide for a sufficient time and under suitable conditions. This may be effected, e.g, by incubation at 6° C. for about 1 to 12 hours, followed by a washing procedure (e.g., using hybridization buffer without PEG), which is then covered with a plastic film and placed against a phosphorimager screen for five minutes to overnight, dependent on the amount of label. Methods for effecting and optimizing hybridization are well known in the art.

As discussed above, the subject attachment method should be applicable for other amino/hydroxyl group-containing compounds, wherein such groups are preferably oriented on adjacent carbon atoms. Other compounds include in particular proteinaceous molecules such as peptides, polypeptides, and proteins, and more specifically, hormones, antibodies, enzymes, and fragments thereof, catalyst molecules, carbohydrates, and other organic compounds. The present invention should be applicable to any compound which desirably is to be attached to a silaceous or silane-containing substrate, e.g., glass, such as a glass slide, quartz, $SiO_2$, micromachined silicon, porous silica, or oxidized silicon material. It is anticipated that optimal attachment conditions for other amino/hydroxyl (non-nucleic acids) will correspond to those described above. This present attachment method should in particular be suitable for attaching an enzyme, antibody or a ligand to a silaceous or silane-containing substrate, such as glass, oxidized silicon, micromachined silicon, or other porous silica to produce an enzyme, antibody or other ligand-bound glass or silica substrates, which may be used for immunopurification or immunodetection. Given the afore-discussed stability of the subject attachment, it is anticipated that these substrates to which are immobilized an enzyme, antibody or a ligand, will be able to be used repeatedly, i.e. without the need to reattach the compound to the substrate after effecting an immunopurification or immunodetection procedure. Thus, the present invention provides for the reusability of the substrate after attachment by removal of the target nucleic acid sequence after a hybridization round has been completed.

In order to further facilitate an understanding of the invention, the following non-limiting Examples are provided.

EXAMPLES

Materials

The following materials were used in the example that follows.

Oligonucleotides

Oligonucleotides were synthesized by Genosys Biotechnologies, Inc. (The Woodlands, Tex.) using standard phosphoramidite chemistry (Matteucci, M. D. and Caruthers, M. H. (1981) *J. Am. Chem. Soc.*, 103, 3185–3191) and the segmented synthesis strategy which permits simultaneous preparation of numerous oligonucleotides (Beattie, K. L., Logsdon, N. J., Anderson, R. S., Espinosa-Lara, J. M., Maldonado-Rodriguez, R. and Frost, J. D. III (1988) *Appl. Biochem. Biotechnol.*, 10, 510–521; Beattie, K. L. and Fowler, R. F. (1991) *Nature*, 352, 548–549; Beattie, K. L. and Hurst, G. D. (1994) in Epton, R. (ed.), *Innovation and Perspectives in Solid Phase Synthesis: Peptides, Proteins and Nucleic Acids—Biological and Biomedical Applications*, West Midlands, England, U.K., pp.69–76). Introduction of 3'-amine function onto oligonucleotides was achieved by use of 3'-Amino-Modifier C3 controlled-pore glass support, obtained from Glen Research (Sterling, Va.) The 5'-aminopropanol function was incorporated into oligonucleotides during the chemical synthesis by the use of 5'-Amino-Modifier C6 phosphoramidite (Glen Research, Sterling, Va.).

Target DNA

To prepare $^{32}$P-labeled oligonucleotide targets, $^{32}$P-labeling was incorporated into the target by the action of polynucleotide kinase in the presence of [γ-$^{32}$P]ATP. Labeled oligonucleotide was loaded onto a Microcon-3 microconcentrator (Amicon, Inc., Beverley, Mass.) and washed three times with water to remove unincorporated [γ-$^{32}$P]ATP. To prepare single-stranded target by the polymerase chain reaction (PCR), amplification was carried out using one PCR primer labeled at the 5'-end with biotin (introduced during the synthesis by use of biotin phosphoramidite) and the other primer was 5'-labeled with $^{32}$P by use of polynucleotide kinase. The amplicon was processed with a Millipore (Bedford, Mass.) Ultrafee spin filter (30,000 MW cutoff) to remove excess PCR primers. The retained material then was applied to an AffiniTip Strep20 column (Genosys Biotechnologies, Inc., The Woodlands, Tex.). The biotin-containing single-stranded eluate from the column was desalted and concentrated by ethanol precipitation.

Example 1

Preparation of Oligonucleotide Arrays

Attachment of terminal amine-derivatized oligonucleotides to epoxysilane-activated glass slides was conducted as described previously. (Beattie et al, *Clin. Chem.*, 41(5), 700–706 (1995); Beattie et al, *Molec. Biotechnol.*, 4:213–225 (1995)). For attachment of 3'-aminopropanol oligonucleotides to plain glass slides the following general procedure was used, except where otherwise indicated. Microscope slides (Fisher) were soaked at room temperature in hexane (10 min), then in absolute ethanol (10 min) and dried at 80° C. for at least 2 hours. The 3'-aminopropanol-derivatized oligonucleotides were dissolved in sterile deionized water at a concentration of 10–20 μM, then 100–200 μL droplets were applied 1–2 mm apart onto a clean, dry glass slide using a Hamilton MicroLab 2200 fluid dispensing system, as previously described. (Beattie et al, *Clin. Chem.*, 41(5), 700–706 (1995); Beattie et al, *Molec. Biotechnol.*, 4:213–225 (1995).) (These references are incorporated by reference in their entirety herein.) After 15 minutes at room temperature, slides were rinsed in deionized water, air dried, and stored dessicated at room temperature.

Example 2

Hybridization of DNA Targets to Oligonucleotide Arrays

Oligonucleotide arrays were prehybridized by soaking them for one hour at room temperature in 10 mM tripolyphosphate, an effective and economical blocking solution for minimizing the non-specific binding of $^{32}$P-labeled target strands to the glass slide. (Beattie et al, *Molec. Biotechnol.*, 4:213–225 (1995)). (This publication is incorporated by reference herein.) Target DNA (PCR product) was dissolved in hybridization buffer [3.3M tetramethylammonium chloride in 50 mM Tris-HCl (pH8), 2 mM EDTA 0.1% SDS and 10% polyethylene glycol-8000] at a concentration of 10–50 fmol strands/μL (10–50 nM), and a minimum of 2,000 cpm/μL in the hybridization mixture. An aliquot of this mixture was pipetted onto the microscope slide (20 μL for an array occupying ⅓ of the slide or 60 μL for the entire slide) and covered with a glass cover slip. The slide was incubated at 6° C. for two hours to overnight, then the slide was washed at room temperature for at least one hour using the same hybridization buffer, in the absence of PEG. The slide was then covered with a plastic film and placed against a phosphorimager screen for five 10 minutes to overnight, depending on the level of labeling.

Example 3

Characterization and Study of Attachment Formed Between Subject Compound and Silane-Containing Substrate Previous methods for producing glass-tethered oligonucleotide arrays for hybridization-based DNA sequence analysis have involved the application of aliquots of 5'- or 3'-amine-derivatized oligonucleotides to epoxysilanized glass surfaces. (Beattie et al, *Clin Chem.*, 39:719–722 (1992); Eggers et al, *In Advances in DNA Sequencing Technology, Proc. SPIE*, pp. 13–26 (1993); Lamture et al, *Nucl. Acids Res.*, 22:2121–2125 (1994); Beattie et al, *Clin. Chem.*, 41(5), 700–706 (1995); Beattie et al, *Molec. Biotechnol.*, 4:213–225 (1995)). (These references are incorporated by reference herein.) The selective covalent reaction between terminal primary amine on the oligonucleotide and epoxy function on the glass resulted in surface densities of $10^{10}$–$10^{11}$ oligonucleotides/mm$^2$) of glass surface, with oligonucleotides spaced about 30–100 Å apart on the surface. 5'-$^{32}$P-labeling of oligonucleotides, used for quantification of attachment densities in these earlier studies, required derivatization of the probes on the 3'-end.

Figure 1:
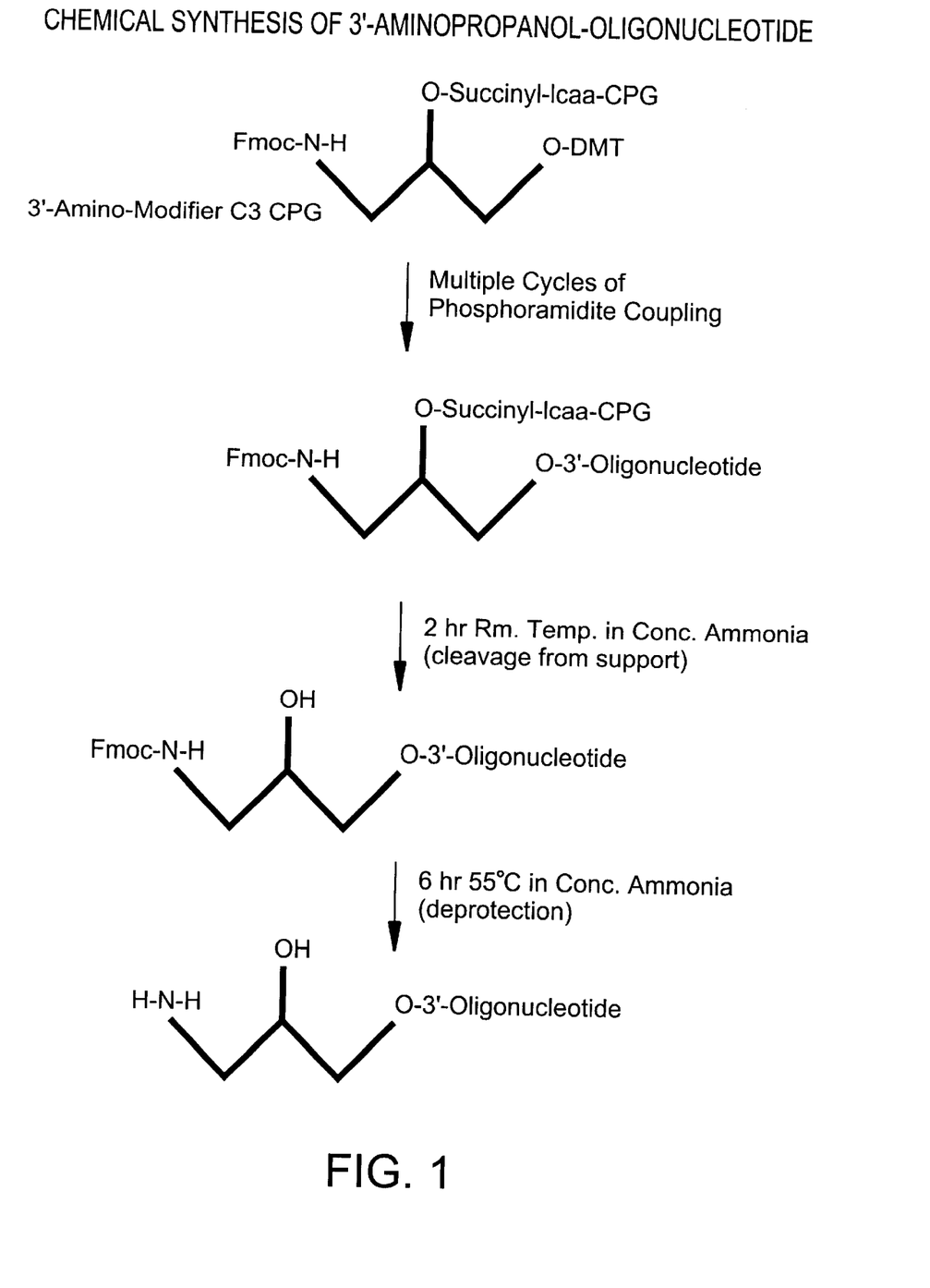
FIG. 1 depicts schematically the synthesis of and contains the structure for a 3'-aminopropanol oligonucleotide suitable for use in the subject method for attaching oligonucleotides to glass and other silanized substrates.

Introduction of the primary amine function onto the 3'-terminus of an oligonucleotide can be conveniently accomplished by use of a special CPG support available from Clontech ("3'-Amine-ON™CPG " or Glen Research ("3'-Amino-Modifier C3 CPG"). During post-synthetic incubation of this support in concentrated ammonia, the Fmoc protecting group is cleaved to generate a primary amine function at the 3'-end of the oligonucleotide, and a 3'-OH group is simultaneously generated by cleavage of the succinate linkage to the glass. Since the pendant amine and hydroxy functions are on carbon atoms 2 and 3 in the C3 linker, the resulting derivatization is actually a 3'-propanolamine or 3'-aminopropanol, as shown in FIG. 1.

This structure differs from the simple aliphatic amine function that is commonly incorporated at the 5'-terminus using C6-amino phosphoramidites in the final coupling reaction during chemical synthesis of oligonucleotides. The terminal amine function was previously shown to be necessary for end-tethering of synthetic oligonucleotides to epoxysilanized class. (Lamture et al, *Nucl. Acids Res.*, 22:2121–2125 (1994); Beattie et al, *Molec. Biotechnol.*, 4:213–225 (1995).) (These references are incorporated by reference herein.)

Figure 2A:
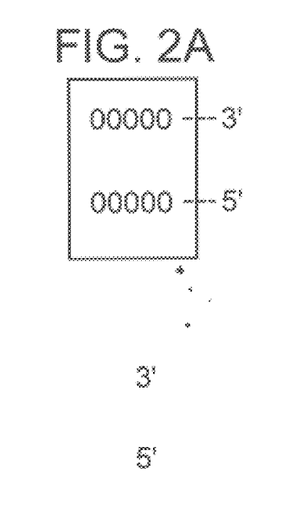
FIG. 2 compares the attachment of 3'-aminopropanol oligonucleotide probes and 5'-amine-derivatized oligonucleotide probes to plain (unactivated or underivatized) glass and epoxysilanized glass. The results show that, of the two, only the 3'-aminopropanol-derivatized oligonucleotide probes stably attached to the plain glass.
Figure 2B:
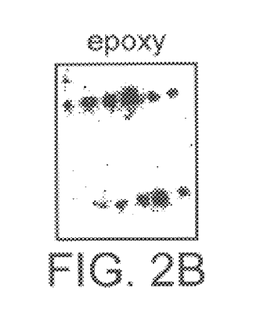
Figure 2C:
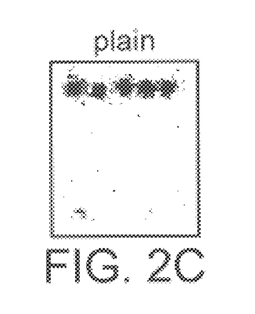

FIG. 2 contains the results of an experiment in which 150-nl droplets of 5'-amino or 3'-aminopropanol nonamers were robotically spotted onto epoxysilanized glass, and onto clean, underivatized glass in the pattern indicated in Panel A of FIG. 2. After incubation at room temperature for two hours, the microscope slides were washed in water, soaked in prehybridization blocking solution, and then 10 hybridized with a complementary 5'-$^{32}$P-labeled oligonucleotide, to give an indication of the relative attachment efficiency of 5'- vs. 3'-amino-derivatized oligonucleotides to the glass. As seen in Panel B of FIG. 2, a similar hybridization intensity occurred with the 5'- and 3'-amino 9-mer probes on the epoxysilane-derivatized glass slide. By contrast, there was little or no hybridization signal in the area where the 5'-amino-derivatized 9-mer had been applied on the underivatized clean glass (Panel C) (FIG. 2). In the area where the 3'-aminopropanol-derivatized 9-mer was applied to the clean glass, however, the hybridization signal was similar to that obtained using the epoxysilanized glass. Thus, whereas the attachment efficiency on epoxysilane-derivatized glass appears to be similar for oligonucleotides containing 5' and 3'-amine function, only the 3'-aminopropanol-derivatized 9-mers attached to plain, clean glass, apparently as efficiently as on epoxysilanized glass.

Figure 3:
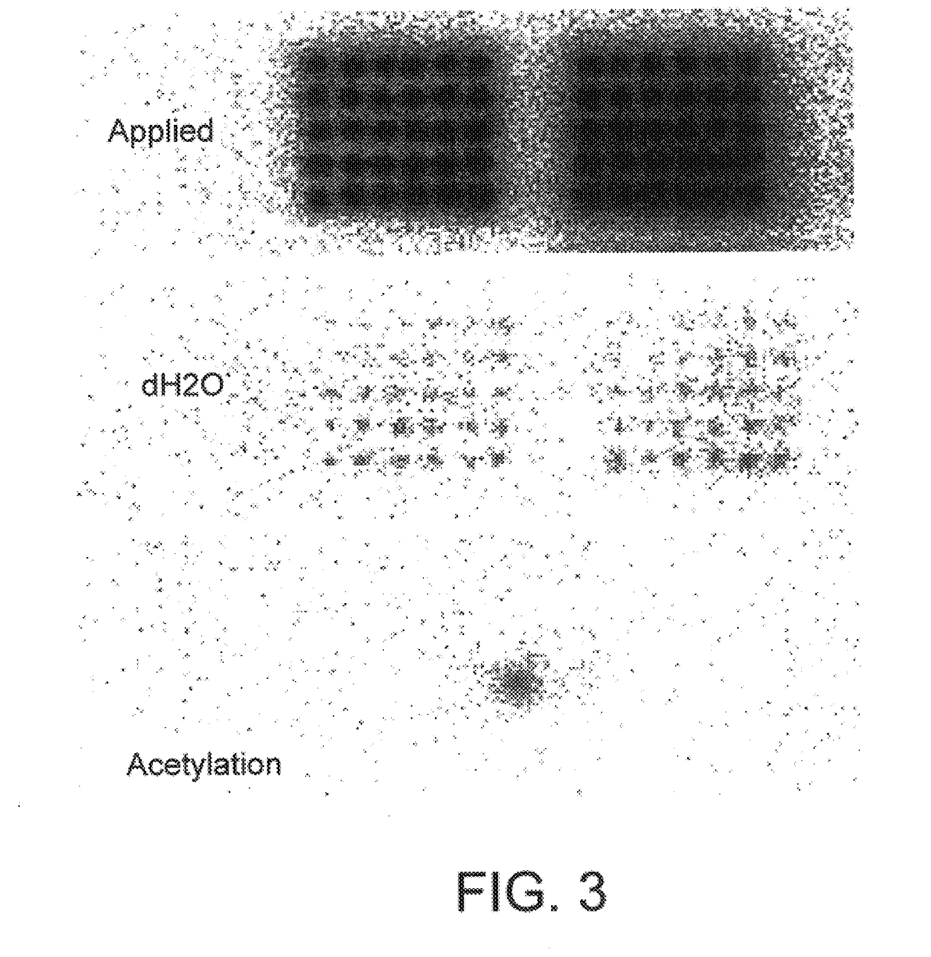
FIG. 3 contains the results of an experiment conducted to evaluate the importance of the amine function on the attachment of the 3'-aminopropanol oligonucleotide to plain glass. In this experiment, the effect of acetylation of the terminal amine on the attachment of 5'-$^{32}$P-labeled aminopropanol-derivatized oligonucleotide to plain glass was evaluated. The results contained in this figure suggest that blockage of the terminal primary amine by acetylation prevented the attachment of the oligonucleotide to the underivatized glass.
Figure 4:
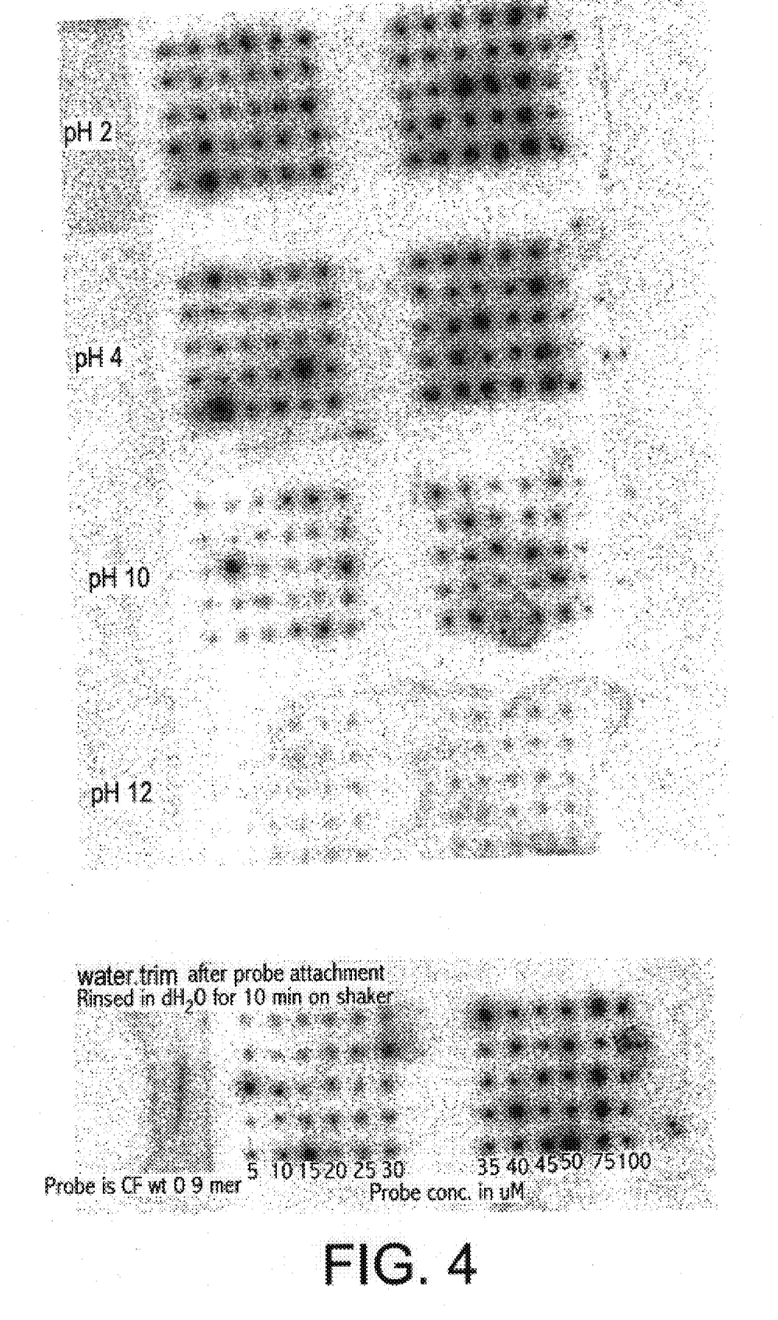
FIG. 4 contains the results of experiments effected to characterize the nature of the stable attachment formed between a 3'-aminopropanol derivatized oligonucleotide and plain glass, by evaluating the stability of the attachment after various post-attachment treatments. Specifically, the effect of pH on the stability of attachment was studied by initially washing a glass plate with distilled water (after effecting the attachment of a 3'-aminopropanol-derivatized oligonucleotide thereto) for two hours, followed by the application of solutions of pH 2, 4, 10, and 12. These results suggest that the attachment between the 3'-aminopropanol oligonucleotide and the plain glass is stable at pH 2 and 4, is slightly labile at pH 10, and is more labile at pH 12.

The results shown in FIGS. 3 and 4 provide some evidence concerning the specific nature of the linkage between 3'-amino probes and plain, underivatized glass. The fact that underivatized (non-amino containing) oligonucleotides did not stably attach to glass according to the procedure described above, (Lamture et al, *Nucl. Acids Res.*, 22:2121–2125 (1994); Beattie et al, *Molec. Biotechnol.*, 4:213–225 (1995) (incorporated by reference herein), and FIG. 6, below)), together with the observation (FIG. 2) that hybridization occurred with aminopropanol-derivatized 9-mer but not with the aliphatic amine-derivatized oligonucleotide applied to plain glass, suggests that neither the amine function, nor the hydroxy function alone is sufficient for attachment to plain glass. Rather, both functional groups are apparently necessary for achieving attachment to plain glass.

In order to further demonstrate the importance of the amine function on attachment, the effect of acetylation of the terminal amine on the attachment of 5'-$^{32}$P-labeled aminopropanol-derivatized oligonucleotide to glass was also evaluated. Specifically, 5'-$^{32}$P-labeled 9 mer probes containing the 3'-aminopropanol function were applied to plain glass slides in five identical rows of 200 nL droplets, at 12 different concentrations between 5 and 100 μM (with constant amount of $^{32}$P label) and dried for two hours. These slides were then washed in distilled water on a shaker for ten minutes.

In addition, $^{32}$P-labeled 9-mer probe with acetyl-blocked amino terminal were well applied to slides, as follows. First, the [$^{32}$P] 9-mer probe with the 3'aminopropanol function was dried in a Speed Vac and dissolved in a 50:50 mixture of pyridine and acetic anhydride. This mixture was allowed to slowly evaporate at room temperature to give the reaction from amine to amide time to complete. The dried DNA was then dissolved in water at approximately 20 pmol/μL, 200 nL droplets of the solution were applied to a slide in two 5×6 groups, allowed two hours to dry, and then washed according to the same procedure as the first two slides.

The phosphorimager data from this experiment are shown in FIG. 3. The phosphorimage of the slide labeled "Applied" represents total probe applied to the glass and dried without washing. The slide labeled "dH20" was washed with water to remove labeled probes that were not covalently attached. The slide labeled "Acetylation" contained probes treated with acetic anhydride prior to application to the glass. The lack of probe attachment following acetylation suggests that the amine function is required for the attachment of aminopropanol-derivatized oligonucleotides to plain glass.

Figure 6A:
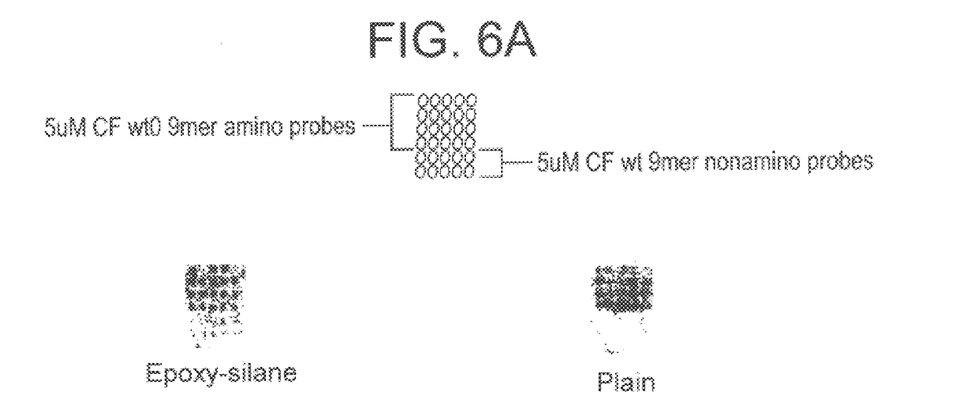
FIGS. 6A–6C contain the results of experiments which compared the hybridization efficiency of 9-mer probes according to the invention (3'-aminopropanol derivatized 9-mers) and underivatized (non-amino) oligonucleotides applied to plain glass and epoxysilanized glass, which were subsequently hybridized to a $^{32}$P-labeled complementary 21-mer target.

In order to further characterize the stability of the attachment formed between 3'-aminopropanol-derivatized oligonucleotides and plain glass surfaces, the stability of the linkage to various post-attachment treatments was studied. Previous studies suggested that the attachment is quite stable (i.e., likely covalent) because repeated rounds of hybridization can be effected using probes attached by the subject method, using hot water to flush away bound target strands between each hybridization step (Doktycz et al, In Beugelsdijk, T. J. (Ed.), *Automation Technologies for Genome Characterization*, John Wiley & Sons, Inc., pp. 205–225 (1997), incorporated by reference in their entirety herein, and FIG. 6, below.))

Specifically, the effect of pH on the stability of the linkage between 200-nL aliquots of $^{32}$P labeled 9-mer and plain glass was studied. These results are contained in FIG. 4. In this experiment five $^{32}$P-labeled, 3'-aminopropanol-derivatized 9-mers were attached to clean glass at concentrations ranging from 5 μM to 100 μM (as in the experiment of FIG. 3), washed for 2 hr with distilled water, then soaked for 30 min. at room temperature with solutions buffered at pH 2, 4, 10 and 12. The bond between oligonucleotide and glass was stable at pH 2 and pH 4, slightly labile at pH 10, and quite labile at pH 12.

Figure 5:
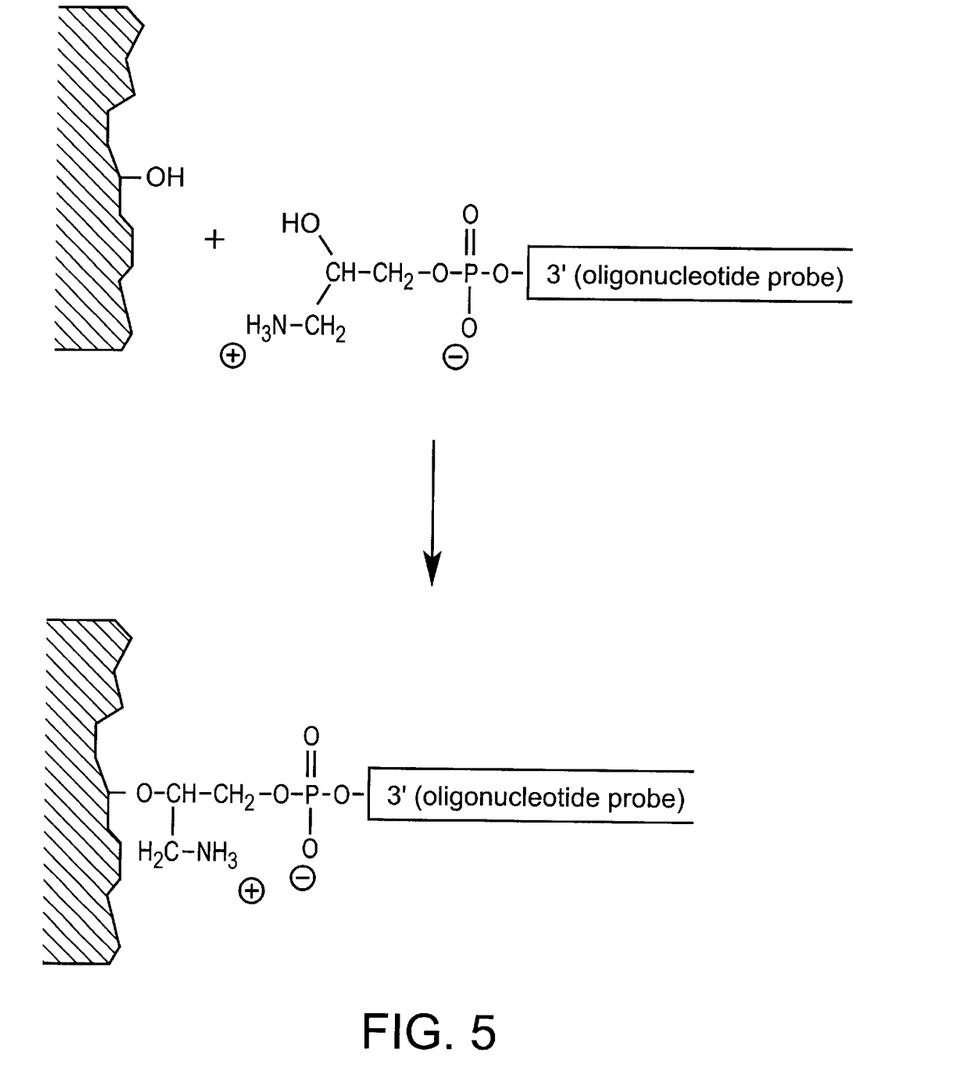
FIG. 5 is a schematic representation of the proposed linkage that is formed between the 3'-aminopropanol derivatized oligonucleotide and the plain glass. It can be seen therefrom that the proposed linkage is a covalent ester linkage.

It is hypothesized by the subject inventor, based on the above-described results, that the bond formed between 3'-aminopropanol-derivatized oligonucleotide and underivatized glass is a covalent bond, more specifically, an ester linkage produced through the hydroxyl group, rather than an amide linkage through the amine. The proposed ester linkage is shown in FIG. 5. However, the present inventor does not wish to be restricted to such hypothesis. Moreover, it is not necessary for an understanding of the invention.

A catalytic function of the amine group is also consistent with the results discussed above. It is also hypothesized by the inventor that a further driving force for the attachment reaction may be formation of a strong salt linkage between the amino group and the adjacent phosphate group, which may stabilize the conformationally constrained end-tethered structure. The involvement of the phosphate group in the attachment reaction is suggested by the observation that pretreatment of the glass with propanolamine (but not propanol) appears to diminish, but not eliminate the subsequent attachment of 3'-aminopropanol oligonucleotide to plain glass (unpublished experiments). The effect of different salt concentrations on attachment and optimal salt concentrations for optimizing the attachment reaction can be determined by one of ordinary skill by trial-and-error experimentation.

Example 4

Comparison of Attachment of Probes to Plain Glass and Epoxysilane Treated Glass Slides Hybridization of 9-mer probes tethered to glass using the two attachment methods was compared. Specifically, the probes (100 nL of 5 μM solution in H$_2$O) were applied to an epoxy-silane treated slide and to a plain slide that was simply washed in 1N HNO$_3$ followed by acetone, hexane and ethanol. The probes were allowed to attach for twenty minutes at room temperature. After drying they were washed in water for fifteen minutes then with 0.2M triethylamine for 15 min followed by another fifteen minutes water wash, allowed to dry, then soaked in 10 mM TPP for one hour. Finally, the probes were hybridized to a complementary $^{32}$P-labeled synthetic 21-mer target overnight at 6° C. The results are shown in FIGS. 6A–6C.

In the experiment depicted in FIG. 6A, aliquots of unlabeled 3'-aminopropanol-derivatized 9-mers were applied to glass in a 5×4 pattern, together with a 5×2 pattern of underivatized (non-amino) oligonucleotides as indicated in the key at the top. These patterns of 9-mers were applied to epoxysilanized glass (lower left) and to clean, underivatized glass (lower right), then hybridized with a $^{32}$P-labeled complementary 21-mer target oligonucleotide, and the hybridization signals were analyzed on a phosphorimager. On the basis of hybridization intensity, the selective attachment of 3'-aminopropanol-derivatized oligonucleotides (compared with non-amino probes) to the glass was clearly evident. However, in the case of epoxysilanized glass, there appeared to be noticeable attachment of underivatized oligonucleotides to the glass.

Figure 6B:
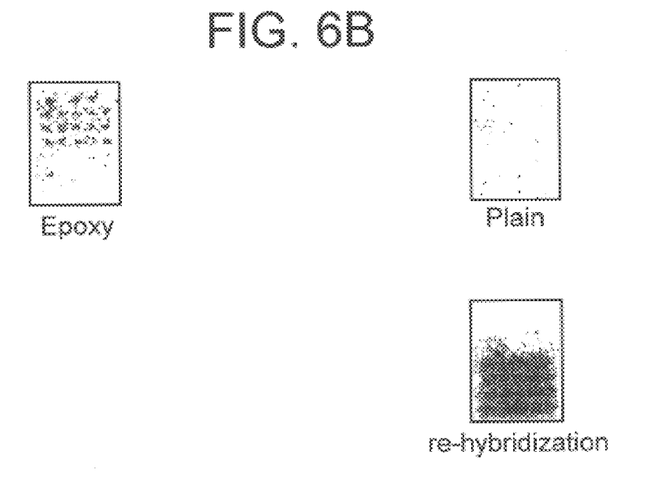
Figure 6C:
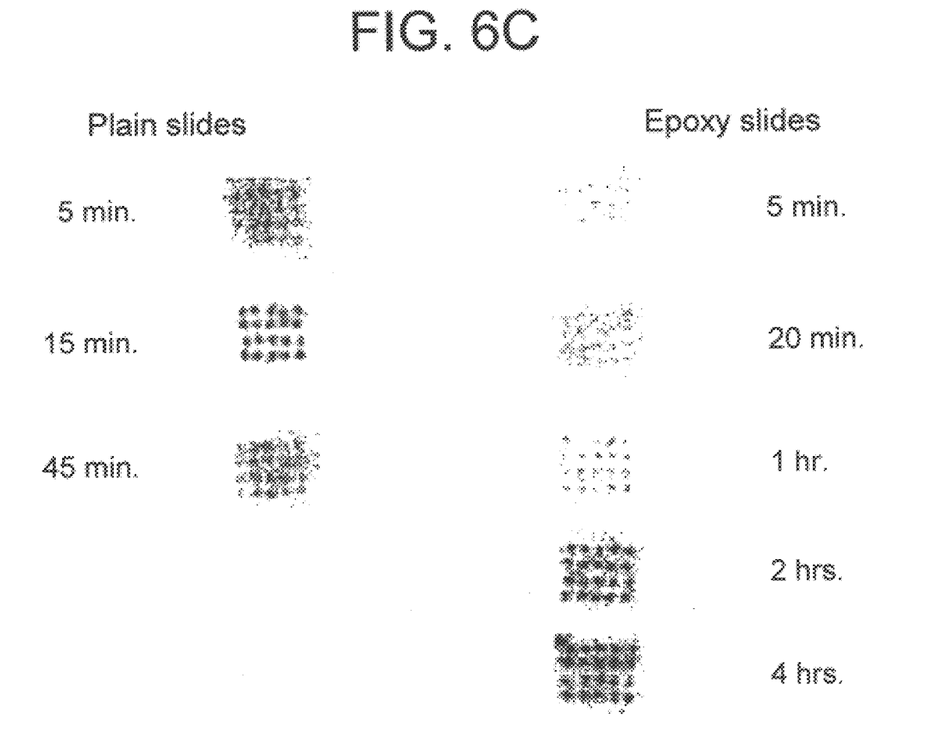

Stripping and rehybridization of the oligonucleotide arrays prepared on epoxysilanized glass vs. plain glass was compared, as depicted in FIG. 6B. The results demonstrated that the plain glass and the epoxysilanized glass yielded a similar hybridization intensity.

While the subject attachment method has numerous benefits, one disadvantage of the use of plain slides is the fact that drops tend to spread more than on the epoxysilanized slides. However, this can be easily remedied by using a 28 gauge needle and keeping the slides extremely dry after cleaning.

Example 5

Multiple Cycles of Hybridization

Plain slides exhibit the ability to be reused for more than one hybridization. The plain slides used for the amino/non-amino discrimination were washed in water at 65° C. for two hours. The hybrids on the plain slides detached, whereas the targets on the epoxy slides remained attached (FIG. 6B).

It seems well established that the probe-target bonding on the glass is via base-pairing. Assuming such means of attachment, the targets should readily wash off in hot water. This is apparently the case with the plain slide. However, there still existed the possibility that both the target and probes were removed. To be certain that the probes are still attached, the plain slide was re-hybridized with $^{32}$P-labeled 21-mer synthetic target, as described supra for the first hybridization. The fact that the hybridization intensity was similar to that obtained in the first round would indicate that the probes remained stably attached to the plain glass substrate after attachment.

Following extensive hot water rinsing of the slides used in FIG. 6A, significant $^{32}$P label remained in the case-of the epoxysilanized glass but not the plain glass slides. Rehybridization of the arrays prepared on plain glass yielded hybridization intensity similar to that in the first round, indicating that the probes remained in place. Therefore, the bond that holds the probe to the slide is very likely covalent in nature, whereas the bond between the probes and target involves reversible H-bonded base pairing in the case of plain glass. With epoxysilane-amine attachment, it is difficult to remove hybridized strands, apparently because of some type of covalent side reaction that occurs following the base pairing.

Also, the hybridization efficiency of a target to plain and epoxysilane glass treated with a probe was compared over time. Slides were prepared with 100 nL drops of 5 μM 9-mer probe, then hybridized with the complement-containing $^{32}$P-labeled 21-mer synthetic target. (FIG. 6B, lower panel.) Probes attached to the plain slides hybridized much faster than those attached to the epoxy-silane slides, as seen in FIG. 6C, which shows the timecourse of hybridization of 9-mer arrays prepared using epoxysilanized vs. plain glass. These results demonstrate that oligonucleotide arrays prepared by the attachment method of the present invention provides for more rapid hybridization than corresponding arrays prepared using epoxysilaned glass.

Thus, the present invention provides a more efficient method for attaching oligonucleotides to glass by certain preferred embodiments. Specifically, it is both faster than prior techniques and simpler because it obviates the need to derivatize or activate the glass prior to attachment. Moreover, the results disclosed herein further indicate that the subject attachment method can yield cleaner attachment/hybridization results and, moreover, provides for highly stable attachment, as evidenced by the fact that it enables multiple rounds of hybridization.

While the invention has been described in terms of preferred embodiments, the skilled artisan will appreciate that various modifications, substitutions, omissions and changes may be made without departing from the spirit thereof.

What is claimed:

1. A method for hybridizing a target nucleic acid sequence to a probe stably attached to an underivatized glass comprising:

(i) contacting a solution of probe with an underivatized glass wherein said probe comprises a composition having at least one amino functional group and at least one hydroxyl functional group separated by at most 1 to 6 atoms;

(ii) allowing stable attachment of said probe to said underivatized containing glass;

(iii) rinsing said glass surface with water to remove unbound probes; and (iv) hybridizing at least one target nucleic acid sequence to said stably attached probe.

2. The method of claim 1, wherein said probe comprises a detectable label that provides for quantitative detection of the probe stably attached to the underivatized glass.

3. The method of claim 2, wherein said detectable label is selected from the group consisting of radionuclides, fluorescent tags, ligands, chemiluminescent tags, enzymes, and chemical groups distinguishable by mass or other spectroscopic properties.

4. The method of claim 3, wherein said radionuclide is selected from the group consisting of $^{32}$P, $^{33}$P and $^{35}$S.

5. The method of claim 1, wherein a prehybridization step is effected prior to hybridization which comprises contacting the glass to which is stably attached said probe with a blocking solution that reduces non-specific binding.

6. The method of claim 1, wherein said target nucleic acid is selected from the group consisting of oligonucleotides, mRNA, cDNA, genomic DNA, and fragments thereof.

7. The method of claim 1, wherein said target nucleic acid comprises a detectable label.

8. The method of claim 7, wherein said detectable label is selected from the group consisting of radionuclides, fluorescent tags, ligands, chemiluminescent tags, enzymes, and chemical groups distinguishable by mass or other spectroscopic properties.

9. The method of claim 8, wherein said radionuclide is selected from the group consisting of $^{32}$P, $^{33}$P and $^{35}$S.

10. The method of claim 1, wherein said probe comprises a composition having at least one amino functional group and at least one hydroxyl functional group separated by at most 1 to 3 atoms.

11. The method of claim 1, wherein said probe comprises a composition having at least one amino functional group and at least one hydroxyl functional group on adjacent atoms.

12. The method of claim 1, wherein said composition having at least one amino functional group and at least one hydroxyl functional group comprises at least one aminopropanol group.

13. The method of claim 1, wherein said probe is selected from the group consisting of an underivatized or derivatized nucleic acid, oligonucleotide, DNA fragment, peptide, protein and polypeptide.

14. The method of claim 13, wherein said probe is a derivatized oligonucleotide.

15. The method of claim 14, wherein said derivatized oligonucleotide is a 3' or 5' aminopropanol derivatized oligonucleotide.

16. The method of claim 1, wherein said target nucleic acid stably hybridizes to said stably attached probe.

17. The method of claim 1, wherein said target nucleic acid removably hybridizes to said stably attached probe.

* * * * *